(12) United States Patent
Kujawski

(10) Patent No.: US 7,887,575 B2
(45) Date of Patent: Feb. 15, 2011

(54) STENT WITH SEGMENTED GRAFT

(75) Inventor: Dennis Kujawski, Warwick, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 991 days.

(21) Appl. No.: 10/153,322

(22) Filed: May 22, 2002

(65) Prior Publication Data
US 2003/0220682 A1     Nov. 27, 2003

(51) Int. Cl.
*A61F 2/06* (2006.01)
(52) U.S. Cl. ..................... 623/1.13; 623/1.14
(58) Field of Classification Search ............... 623/1.13, 623/1.23, 1.35, 1.44, 1.14, 1.15, 1.16
See application file for complete search history.

(56) References Cited

U.S. PATENT DOCUMENTS

| | | | | |
|---|---|---|---|---|
| 5,522,822 A * | 6/1996 | Phelps et al. | ................. | 606/191 |
| 5,628,783 A * | 5/1997 | Quiachon et al. | ........... | 623/1.35 |
| 5,800,512 A * | 9/1998 | Lentz et al. | ................... | 623/1.1 |
| 5,824,040 A * | 10/1998 | Cox et al. | ................... | 623/1.35 |
| 5,843,164 A | 12/1998 | Frantzen et al. | | |
| 5,919,224 A * | 7/1999 | Thompson et al. | .......... | 606/194 |
| 5,954,764 A * | 9/1999 | Parodi | ....................... | 623/1.11 |
| 5,989,276 A * | 11/1999 | Houser et al. | ................ | 606/170 |
| 6,099,558 A * | 8/2000 | White et al. | ................ | 623/1.16 |
| 6,156,064 A * | 12/2000 | Chouinard | ................. | 623/1.44 |
| 6,254,627 B1 * | 7/2001 | Freidberg | .................. | 623/1.11 |
| 6,264,684 B1 * | 7/2001 | Banas et al. | ................ | 623/1.13 |
| 6,270,525 B1 * | 8/2001 | Letendre et al. | ............ | 623/1.35 |
| 6,364,904 B1 * | 4/2002 | Smith | ........................ | 623/1.22 |
| 6,398,802 B1 | 6/2002 | Yee | | |
| 6,626,939 B1 | 9/2003 | Burnside et al. | | |
| 6,773,456 B1 * | 8/2004 | Gordon et al. | ............. | 623/1.28 |

(Continued)

FOREIGN PATENT DOCUMENTS

EP     0 923 912 A2     6/1999

(Continued)

OTHER PUBLICATIONS

International Search Report corresponding to International Patent Application PCT/US03/10502, mailing date Dec. 2, 2003.

(Continued)

*Primary Examiner*—Anhtuan T Nguyen
*Assistant Examiner*—Amy Lang
(74) *Attorney, Agent, or Firm*—Brooks, Cameron & Huebsch, PLLC

(57) ABSTRACT

A stent-graft comprising an expandable stent and a plurality of graft segments, each graft segment having a first end attached to the stent and a second end not attached to the stent. In one embodiment, the plurality of overlapped graft segments form a continuous conduit wherein each overlap between axially adjacent graft segments comprises a fluid-tight seal when the stent in the radially expanded configuration sandwiches the graft segments against a wall of a body lumen. In another embodiment, there are one or more discontinuities in the plurality of graft segments. The discontinuities may be aligned with branch lumens. The graft segments may be cut perpendicular to the stent-graft axis, or on a bias. A delivery system for and method of deploying the stent-graft are also claimed.

28 Claims, 3 Drawing Sheets

U.S. PATENT DOCUMENTS

| | | | |
|---|---|---|---|
| 6,800,089 B1 * | 10/2004 | Wang | 623/1.13 |
| 7,018,401 B1 * | 3/2006 | Hyodoh et al. | 623/1.12 |
| 2004/0133266 A1 * | 7/2004 | Clerc et al. | 623/1.22 |

FOREIGN PATENT DOCUMENTS

| | | |
|---|---|---|
| EP | 0 923 912 A3 | 6/1999 |
| JP | 11-197252 | 7/1999 |
| JP | 11-512635 | 11/1999 |
| WO | 97/12562 | 4/1997 |
| WO | WO 98/27895 | 7/1998 |
| WO | WO 99/15105 | 4/1999 |
| WO | WO 99/25271 | 5/1999 |
| WO | WO 00/78248 | 12/2000 |
| WO | WO 00/78248 A1 | 12/2000 |

OTHER PUBLICATIONS

U.S. Appl. No. 09/442,165, filed Nov. 16, 1999, for the invention of Paul F. Chouinard et al.

U.S. Appl. No. 09/702,226, filed Oct. 31. 2000, for the invention of Steven E. Walak.

U.S. Appl. No. 10/115,669, filed Apr. 4, 2002, for the invention of James Weldon et al.

Japanese Office Action for Application No. JP 2004-506689 mailed Mar. 13, 2009 (w/English translation).

An Official Action and English translation from related Japanese Patent Application No. 2004-506689, dated Nov. 6, 2009. 5 pages.

* cited by examiner

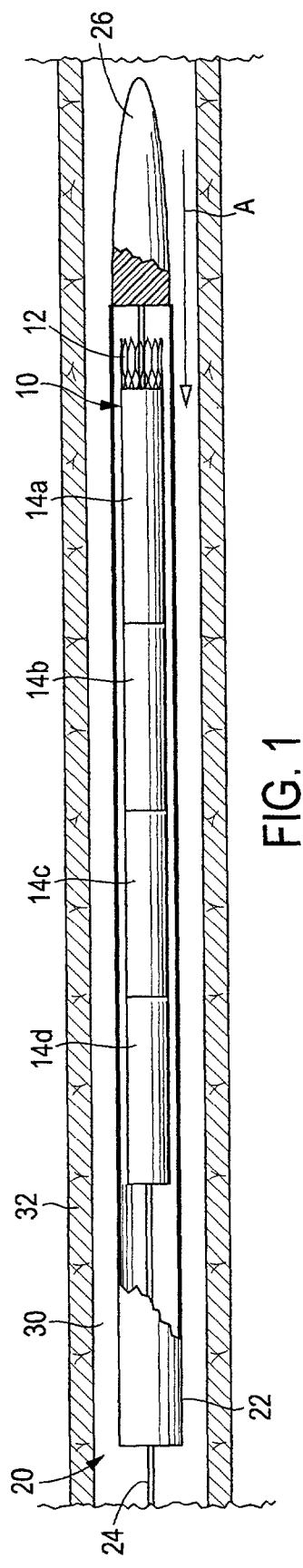
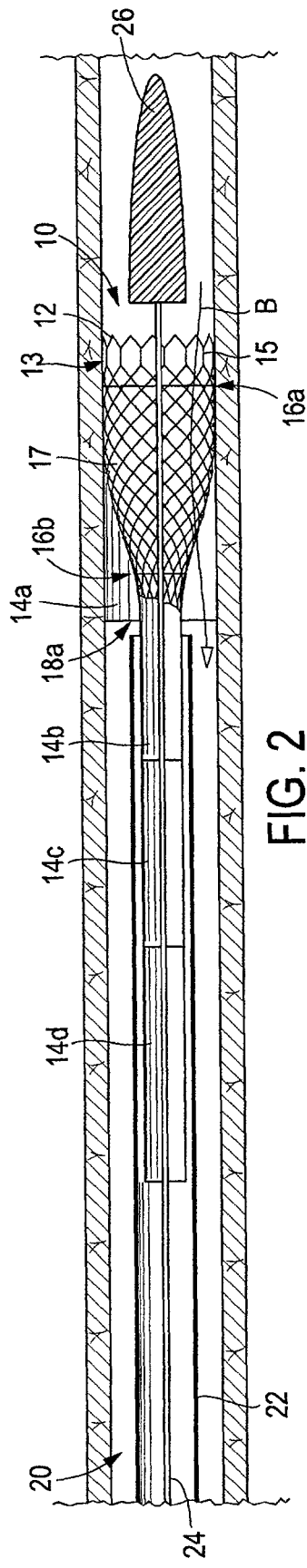
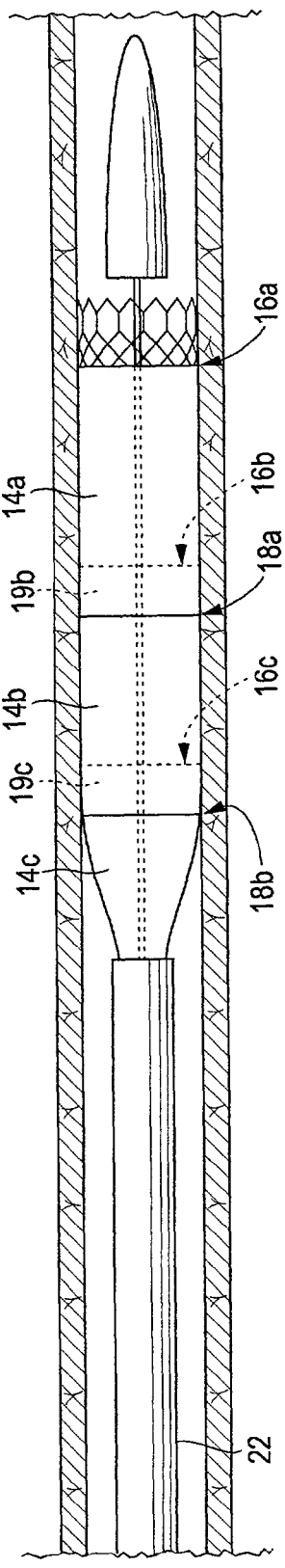

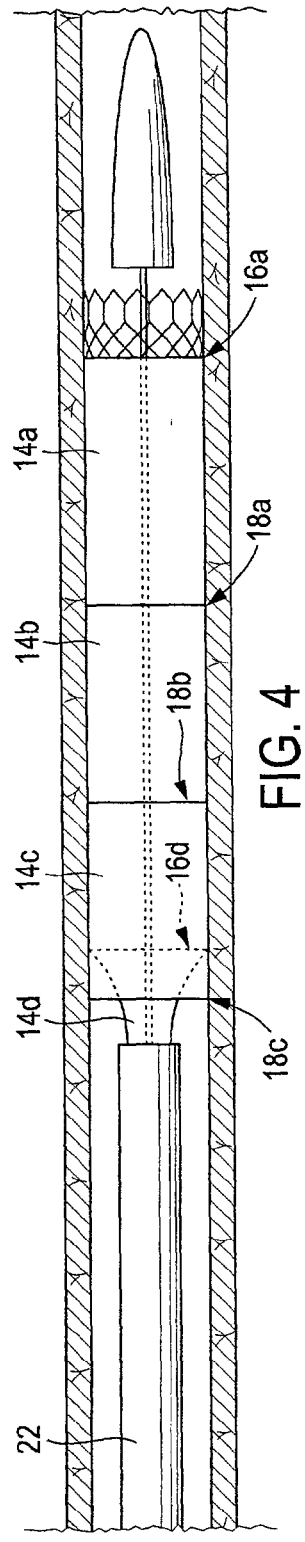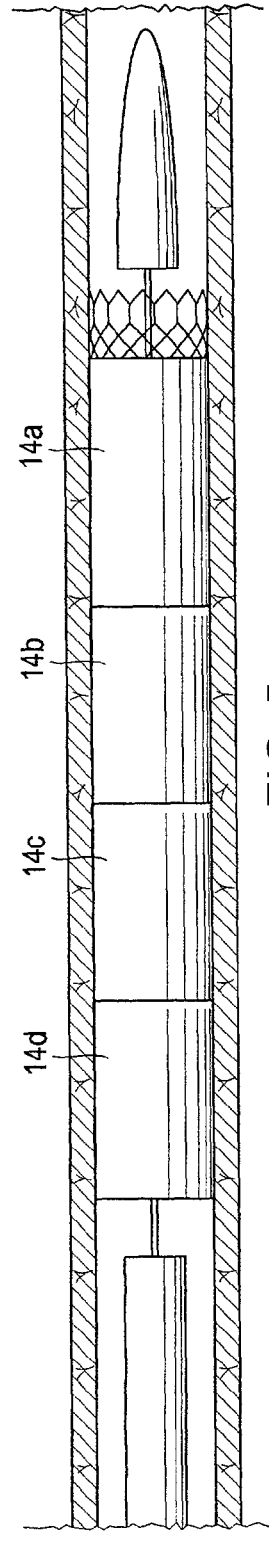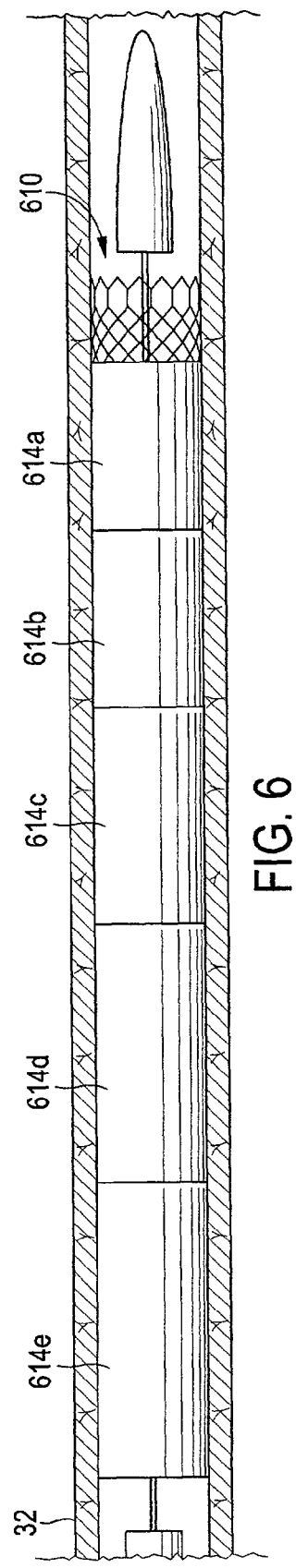

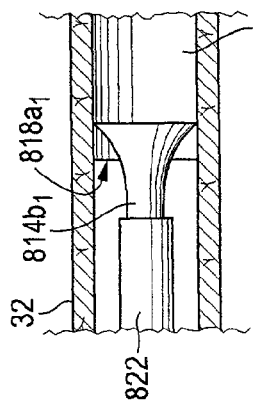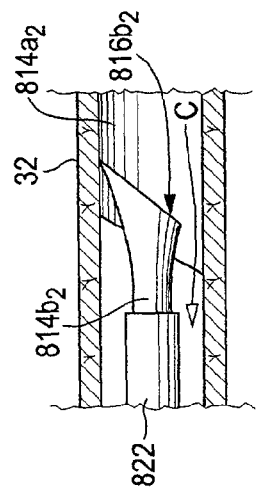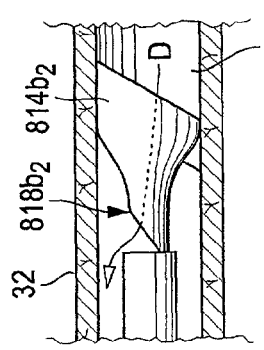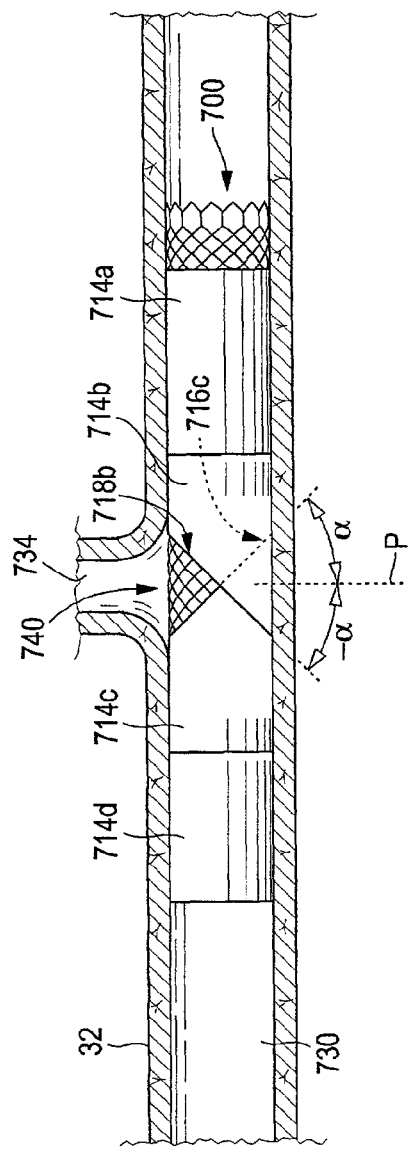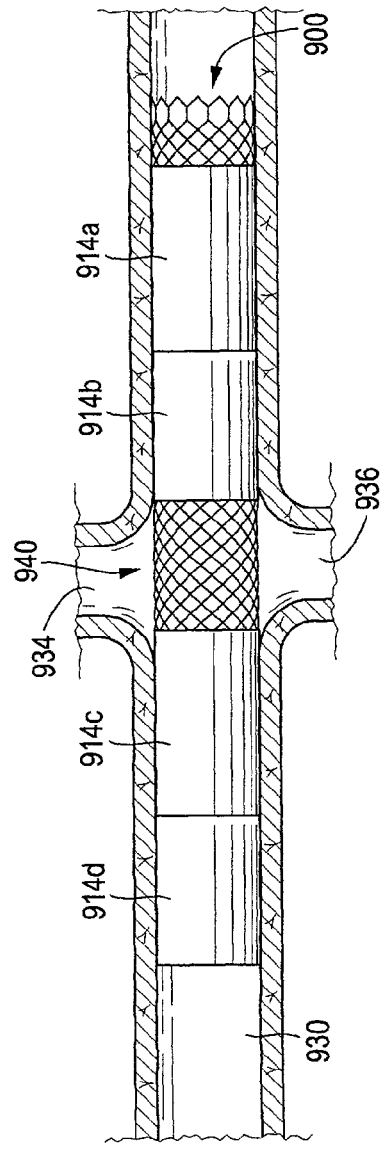

STENT WITH SEGMENTED GRAFT

TECHNICAL FIELD

The present invention relates generally to endoluminal grafts or "stents" and, more specifically, to stent-graft combinations adapted to be deployed without interrupting fluid flow during deployment.

BACKGROUND OF THE INVENTION

A stent is an elongated device used to support an intraluminal wall. In the case of a stenosis, a stent provides an unobstructed conduit through a body lumen in the area of the stenosis. Such a stent may also have a prosthetic graft layer of fabric or covering lining the inside and/or outside thereof. Such a covered stent is commonly referred to in the art as an intraluminal prosthesis, an endoluminal or endovascular graft (EVG), or a stent-graft. A stent-graft may be used, for example, to treat a vascular aneurysm by removing the pressure on a weakened part of an artery so as to reduce the risk of rupture. The term "endoluminal device" is often used to refer to any device implanted in a lumen, including stents, stent-grafts, vena cava filters, and the like.

Typically, an endoluminal device, such as a stent-graft deployed in a blood vessel at the site of a stenosis or aneurysm, is implanted endoluminally, i.e. by so-called "minimally invasive techniques" in which the device, restrained in a radially compressed configuration by a sheath or catheter, is delivered by a delivery system or "introducer" to the site where it is required. The introducer may enter the body from an access location remote from the treatment site, such as through the patient's skin, or by a "cut down" technique in which the entry blood vessel is exposed by minor surgical means. The term "proximal" as used herein refers to portions of the stent or delivery system relatively closer to the end of the delivery system that is remote from the treatment site, whereas the term "distal" is used to refer to portions farther from the end that is remote from the treatment site.

When the introducer has been advanced into the body lumen to the deployment location, the introducer is manipulated to cause the endoluminal device to be ejected from the surrounding sheath or catheter in which it is restrained (or alternatively the surrounding sheath or catheter is retracted from the endoluminal device), whereupon the endoluminal device is expanded to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Stent-grafts are known in the art having a "wind-sock" design whereby the graft is attached to the stent at only an upstream location on the stent, so that as the stent is deployed, endoluminal fluid can continue to flow between the stent and the graft, while the graft is suspended like a wind sock. Such designs avoid the pressure of obstructed blood flow during deployment that may cause the prosthesis to migrate away from its intended location or become longitudinally compressed. An exemplary such stent-graft design is described in U.S. Pat. No. 5,954,764 to Juan Parodi, incorporated herein by reference, which also describes an exemplary device for deploying such a stent-graft design. Another deployment system for such a stent-graft design is described in U.S. patent application Ser. No. 09/337,120, titled LOW PROFILE DELIVERY SYSTEM FOR STENT AND GRAFT DEPLOYMENT AND METHOD FOR DEPLOYMENT, by Carl E. Yee, filed Jun. 21, 1999, assigned to the assignee of the present invention, and incorporated herein by reference.

The standard wind-sock stents known in the art, however, have drawbacks related to precision of deployment, stent flexibility once deployed, and complexity of the introducers used for deploying them. Thus, there is still a need in the art for improved stent-graft designs that minimize disruption of fluid flow during deployment, but also provide advantages over designs currently known in the art.

SUMMARY OF THE INVENTION

One aspect of the invention comprises a stent-graft comprising an expandable stent and a plurality of graft segments, each graft segment having a first end attached to the stent and a second end not attached to the stent. In one embodiment, the graft segments radially overlie the stent, forming one or more overlaps between axially adjacent graft segments. Each graft segment second end may radially overlie the first end of an axially adjacent graft segment, the graft segment first end may radially underlie a second end of another axially adjacent graft segment, or both. In one embodiment, the plurality of overlapped graft segments form a continuous conduit wherein each overlap between axially adjacent graft segments comprises a fluid-tight seal when the stent in the radially expanded configuration sandwiches the graft segments against a wall of a body lumen. In another embodiment, there are one or more discontinuities in the plurality of graft segments.

All of the plurality of graft segments may have an equal length, or one or more graft segments may be relatively shorter than one or more other graft segments. The relatively shorter-length graft segments may be aligned with the curved or tortuous portion of the body lumen, or may be positioned upstream of the one or more relatively longer graft segments.

Each of the one or more overlaps between axially adjacent graft segments may comprise an overlap along an entire periphery of the stent-graft, or one or more of the overlaps may be along less than an entire periphery of the stent-graft. Each graft segment may have opposite ends that are perpendicular to the central axis of the stent-graft, or one or more or all of the graft segments may be biased to the central axis.

The graft segment bias may create a discontinuity in the plurality of graft segments, such as for aligning with a branch lumen or for permitting perfusion. A gap between axially adjacent graft segments may also be provided for creating a discontinuity in the plurality of graft segments.

In one embodiment, the stent-graft is adapted for deployment inside a body lumen in a distal deployment location from a proximal access location outside the body lumen, and the prosthesis comprises or consists of a plurality of graft segments each having a distal end and a proximal end, an expandable stent underlying the graft, a plurality of links at or near the distal end of each graft segment for linking the stent and the graft segments together, and a lapped interface between at least one pair of axially adjacent graft segments. The proximal end of a distal graft segment axially overlaps the distal end of a proximal graft segment in each lapped interface.

In another embodiment, the stent-graft is adapted for deployment inside a body lumen having fluid therein that flows downstream from an upstream location to a downstream location. Such a stent-graft comprises an expandable stent and a plurality of graft segments overlying the stent. Each segment has an upstream end and a downstream end, and is linked to the stent only at or near the upstream end. Each graft segment has a downstream end that overlaps the upstream end of an axially adjacent graft segment, an upstream end overlaps the downstream end of an axially adjacent graft segment, or both. In other words, the stent-graft comprises the stent and a first graft segment having an upstream end and a downstream end, the first graft segment attached to the stent only at the first graft segment upstream end. The second graft segment has an upstream end and is attached to the stent only at the second graft segment upstream end in a location on the stent that is upstream of the downstream end of the first graft segment, such that the first graft segment downstream end overlaps the first graft segment upstream end.

Another aspect of the invention is a delivery system for deploying a stent-graft inside a body lumen having fluid therein that flows downstream from an upstream location to a downstream location. The delivery system comprises a stent graft having a compressed configuration and an expanded configuration, the stent-graft comprising an expandable stent and a plurality of graft segments overlying the stent, each graft segment having a first end attached to the stent and a second end not attached to the stent. The delivery system further comprises an outer sheath that overlies the compressed stent-graft and is retractable in the downstream direction. The delivery system may further comprise a shaft mounted coaxially within the outer sheath and a catheter tip on the upstream end of the shaft, the shaft and the catheter tip both optionally having a guidewire lumen therethrough.

Another aspect of the invention is a method for delivering a stent-graft into a body lumen having an intraluminal fluid therein flowing in a downstream direction from an upstream location. The method comprises introducing a delivery system as described herein into the body lumen and retracting the outer sheath in the downstream direction such that when a first graft segment is at least partially unsheathed, the intraluminal fluid flows in a first path through the stent and between the downstream end of the first graft segment and the upstream end of the outer sheath. The fluid flows in this path until an upstream end of a second graft segment is unsheathed sufficiently to cut off flow through the first path. The intraluminal fluid then flows through a second path through the stent between the downstream end of the second graft segment and the outer sheath when the second graft segment is completely unsheathed. The method comprises continuing to retract the outer sheath until the stent-graft is fully deployed. In one embodiment, the plurality of graft segments overlap one another to create a fluid tight seal at each interface between overlapping graft segments, creating a continuous fluid conduit. In another embodiment, the stentgraft comprises one or more discontinuities and the body lumen comprises one or more branch lumens, the method comprising deploying the stent-graft so that the one or more discontinuities are aligned with the one or more branch lumens.

It is to be understood that both the foregoing general description and the following detailed description are exemplary, but are not restrictive, of the invention.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 1 shows an exemplary stent-graft loaded in an exemplary delivery system, shown in partial longitudinal-section, after introduction into a body lumen, shown in longitudinal section;

FIG. 2 shows a complete longitudinal section of the delivery system and stent-graft of FIG. 1 after deployment of a first graft segment;

FIG. 3 shows a plan view of the delivery system and stent-graft of FIG. 1 after deployment of two graft segments inside the lumen;

FIG. 4 depicts the delivery system and stent-graft of FIG. 3 after deployment of three graft segments;

FIG. 5 depicts the delivery system and stent-graft of FIG. 4 after full deployment of the stent-graft;

FIG. 6 shows a plan view of a stent-graft having unequal graft segments inside a longitudinal section of a lumen;

FIG. 7 shows a plan view of a stent-graft having graft segments with biased ends inside a longitudinal section of a lumen having a branch lumen;

FIG. 8A shows a partial longitudinal section of a perpendicular graft segment end being deployed;

FIG. 8B shows a partial longitudinal section of an upstream biased graft segment end being deployed;

FIG. 8C shows a partial longitudinal section of a downstream biased graft segment end being deployed; and FIG. 9 shows a plan view of stent-graft having a discontinuity between two axially adjacent graft segments.

DETAILED DESCRIPTION OF INVENTION

Referring now to the drawing, wherein like reference numerals refer to like elements throughout, FIGS. 1-5 show an exemplary stent-graft 10 of the present invention being deployed from an exemplary delivery system 20 in a distal location in a body lumen 30 from a proximal location outside the body. Intraluminal fluid, such as blood in a vascular application, flows downstream in the direction of arrow A. Stent graft 10 comprises an expandable stent 12 and a plurality of graft segments 14a-14d radially overlying the stent. Each graft segment 14a-14d has its respective distal, upstream end 16a-16d attached to the stent and its proximal, downstream end 18a-18d unattached to the stent. Thus, as shown in FIG. 2, as outer sheath 22 is retracted and graft segment 14a is fully unsheathed, the intraluminal fluid can flow in a path along arrow B through stent 12 and between graft 14a and the upstream end of outer sheath 22.

As shown in FIG. 3, graft segment 14b radially overlaps axially adjacent graft segment 14a along overlapped portion 19b. In particular, the downstream end 18a of graft segment 14a radially overlies upstream end 16b of graft segment 14b. Similarly, the upstream end 16b of graft segment 14b radially underlies downstream end 18a, while the downstream end 18b of graft segment 14b radially overlies upstream end 16c of graft segment 14c. Thus, each graft segment has a downstream end overlying the upstream end of an axially adjacent graft segment (i.e. segments 14a-14c), an upstream end underlying the downstream end of another axially adjacent graft segment (i.e. segments 14b-14d) or both (i.e. 14b and 14c).

The plurality of overlapped graft segments shown in FIGS. 1-5 thus form a continuous conduit, each overlap between axially adjacent graft segments forming a fluid-tight seal as radially expanded stent 12 sandwiches graft segments 14a-d against wall 32 of body lumen 30.

The graft may be a braided or non-braided graft, and may comprise any graft material known in the art. Suitable graft materials include, but are not limited to, polyethyleneterepthalate (PET), polyetheretherketone (PEEK), polysulfone, polytetrafluoroethylene (PTFE), expanded polytetrafluroethylene (ePTFE), fluorinated ethylene propylene (FEP), polycarbonate urethane, a polyolefin (such as polypropylene, polyethylene, or high density polyethylene (HDPE)), silicone, and polyurethane. Yarns for braided grafts may comprise monofilaments or multifilament yarns, either with round or non-round cross-section, and multifilament yarns may comprise twisted or untwisted filaments.

The stent may comprise any material known in the art, including but not limited to self-expanding metals such as nitinol, balloon-expandable materials such as stainless steel, or even non-metals, such as polymer materials. The stent may also comprise a hybrid self-expanding, balloon-expandable design, having at least one superelastic section and at least one plastically deformable section, such as but not limited to those described in U.S. patent application Ser. No. 09/702,226, by Steven E. Walak, filed Oct. 31, 2000, assigned to the common assignee of this invention, and incorporated herein by reference. The stent may comprise any stent architecture known in the art, such as but not limited to filamentary or cut tube architectures, including filamentary stents that are wound or braided along their entire length, or hybrid braided/wound stents, such as are described in U.S. patent application Ser. No. 09/442,165, filed Nov. 16, 1999, by Chouinard et al., assigned to the assignee of this invention and incorporated by reference.

A portion of the underlying stent may be uncovered by graft material at the proximal and/or distal ends of the stent, such as uncovered portion 13 of stent 12 shown in FIGS. 2-5. Such an uncovered stent portion typically allows intraluminal tissue growth (not shown) to provide additional anchoring for the stent as is known in the art. Even where there is no uncovered stent portion at the proximal end, it is desirable for the proximal end of the proximal-most graft (such as graft 14d shown in FIG. 5) not to extend proximally any further than the proximal end of the underlying stent. The ability to better control the terminal location of the proximal end of the graft relative to the proximal end of the stent is one advantage of the segmented covering as compared to non-segmented "windsock" designs, because the unattached portion of the graft is smaller in the segmented design. Accordingly, placement of the proximal end of a segmented graft is easier to predict than placement of the proximal end of a non-segmented graft, taking into account foreshortening of the stent and other factors.

As shown in FIG. 1, stent 12 comprises a hybrid stent having a non-braided distal end section 15 and a braided midsection 17, such as a hybrid wound/braided design as described in the '165 application. The term "midsection" as used herein refers to any portion of the stent-graft between the proximal and the distal ends. Although hybrid stents in which the wound end section and braided midsection are connected by one or more continuous filaments running through both sections as disclosed in the '165 application are advantageous, the invention is not limited to such a configuration, nor is the invention limited to any particular type of stent architecture. The end section may comprise ends that are freely terminating or twisted together, or atraumatic ends such as continuous ends or wound ends, all of which are known in the art. Architectures with continuous ends, for example, are described in publication WO 99/25271 to Wolfgang et al., incorporated herein by reference. End section 15 is not limited to any particular architecture, however, and may comprise any architecture known in the art, including the same architecture as midsection 17.

The attachments or links (not shown) between each graft segment 14a-14d and stent 12 may comprise any type of attachment known in the art, including but not limited to, sutures, staples, adhesive, wire, a sewn seam, and any combination or equivalent thereof.

The stent-graft of this invention may be useful in any number of applications in any body lumen, vascular or non-vascular. In particular, however, it is useful for treatment of thoracic aortic aneurysms (TAA). The segmented graft design is particularly useful for TAA applications because it overcomes the imprecision of existing systems that occlude blood flow during deployment and thus are prone to deployment migration. The pulsatile blood flow in the thoracic aorta may make TAA stent-grafts particularly subject to such migration. The segmented covering as described herein allows blood to flow through each graft segment until the next segment is deployed. The segmented graft design is also advantageous for deployment in any tortuous or curved lumen, thus also providing further advantage for TAA applications.

In stent-graft 10 shown in FIGS. 1-5, the plurality of graft segments comprise a continuous fluid conduit wherein each pair of overlapping graft segments comprises an overlap along a complete periphery of the graft segment, each graft segment has square edges perpendicular to the central axis of the stent-graft (which runs coaxial with shaft 24 shown in FIGS. 1-5), and all the graft segments are of approximately equal length. Any number of variations from this design are possible, however, well-within the scope of this invention. For example, the graft segments may be of unequal length, as illustrated in FIG. 6. One advantage of making graft segments of unequal length is that a section of the stent-graft having more graft segments may have more flexibility than a section with fewer graft segments. Thus, portions of a stent-graft having short graft segments may be particularly well-suited for deployment in curved or tortuous regions of a body lumen.

Stent-graft 610 shown in FIG. 6 balances one advantage of the segmented graft, namely that it allows blood to continue to flow during deployment, against one disadvantage, namely that each overlap between grafts provides a seam that may potentially leak. Stent-graft 610 has upstream graft segments 614a and 614b that are relatively shorter than downstream graft segments 614d and 614e. Graft segments of intermediate length, such as segment 614c, may be provided between the upstream and downstream graft segments, creating a gradient in graft segment length from upstream to downstream ends of the stent-graft. Relatively shorter upstream graft segments 614a and 614b provide less resistance to blood flow at the beginning of deployment when very little of stent-graft 610 has been anchored and it is particularly prone to migration. Relatively longer downstream graft segments 614d and 614e provide fewer seams near the end of deployment when the stent is already partially anchored and more resistant to migration.

In another stent-graft embodiment, the graft segments and/or the stent may be cut on a bias rather than having square edges. In particular, the graft segments may be cut on a bias in such a way as to leave a discontinuity in the stent-graft to accommodate branch lumen. For example, as shown in FIG. 7, lumen 730 has a branch lumen 734, and stent-graft 700 has a discontinuity 740 of graft covering aligned with the branch lumen. Discontinuity 740 is formed by the biased downstream end 718b of graft segment 714b and opposingly-biased upstream end 716c of graft segment 714c. By "opposingly-biased" it is meant that if the relationship between the upstream end and a plane P perpendicular to the central axis of the stent-graft is a positive angle, such as α, then the relationship between the downstream end and plane P is a negative angle, such as −α. Such opposingly-biased graft segments that create a discontinuity inherently overlap each other over less than a full periphery of the graft segment. Accurate placement of discontinuity 740 may be facilitated by the use of radiopaque markers as are known in the art. Acuurate placement of the discontinuity may be further facilitated by the use of non-foreshortening or lesser-foreshortening stent architectures as are known in the art, or by the use of special deployment devices for the deployment of foreshortening endoluminal devices, such as are described in U.S. patent application Ser. No. 10/115,669, titled DELIVERY SYSTEM AND METHOD FOR DEPLOYMENT OF FORESHORTENING ENDOLUMINAL DEVICES, filed by James Weldon and Ilya Yampolsky on Apr. 4, 2002, and incorporated herein by reference.

Although the embodiment shown in FIG. 7 depicts angles α and −α with the same absolute value, the angles may have different absolute values. Overlapping grafts may also have a bias in the same direction (both positive, or both negative), with enough difference in the bias to form a discontinuity. It should be noted that a discontinuity may be provided in a graft by other means, such as merely by cutting out a notch or other type of opening of any shape at the end or middle of a graft segment.

Even where it is not desired to have a discontinuity in the plurality of graft sections, the grafts may be biased, such as to create an elliptical attachment periphery that is greater than the circular attachment periphery provided by a perpendicular end. A larger peripheral attachment area provides greater attachment strength. Biased graft segments may be particularly advantageous for maximizing the percentage of time during deployment that blood can flow through the stent-graft without obstruction. For example, as illustrated in FIG. 8A, perpendicularly-cut graft segment $814b_1$ cuts off flow between downstream end $818a_1$ of graft segment $814a_1$ and outer sheath 822 once the underlying stent becomes sufficiently expanded, and does not allow flow again until graft segment $814b_1$ is completely unsheathed. By comparison, a biased graft segment $814b2$ allows blood to flow longer through path C before it is cut off when the downstream-most portion of upstream end $816b_2$ finally deploys, as shown in FIG. 8B. The biased design also allows blood flow to be reestablished sooner through path D when the upstream-most portion of downstream end $818b2$ of segment $814b_2$ is unsheathed, as shown in FIG. 8C.

In yet another embodiment, shown in FIG. 9, stent-graft 900 may have a discontinuity in the succession of graft segments created by space 940 between axially adjacent graft segments 914b and 914c. Such a discontinuity may be particularly advantageous to accommodate lumens such as lumen 930 having a plurality of branch lumens 934 and 936.

Delivery system shown in FIGS. 1-5 comprises stent graft 10, outer sheath 22, shaft 24, and catheter tip 26 attached to the shaft. Shaft 24 and catheter tip 26 may have lumens (not shown) therein, such as an axial lumen, for accommodating a guidewire (not shown) as is commonly known in the art. The delivery system of the present invention may be used with or without a guidewire. One advantage of the delivery system embodiment shown in FIGS. 1-5 is that the inside portion that actually is introduced into the body lumen is simple, consisting of essentially nothing more than the components shown and described herein, with the guidewire and guidewire lumens in shaft 24 and 26 being optional. Such a simple design avoids the profile-adding multiple sheaths or other complexities of other delivery systems known in the art. Of course, the delivery system may have additional elements not shown herein, as are known in the art. In particular, the delivery system may comprise elements such as luer fittings and the like at the proximal end of the delivery system as are known in the art, that, while in many cases essential to stent delivery procedures generally, are not essential to the discussion herein.

In addition to the structural aspects of the invention, one aspect of the invention is a method for delivering a stent-graft of the type discussed herein into a body lumen. Such a method comprises, with respect to FIGS. 1-5, introducing a delivery system 20 into the body lumen 30, the delivery system comprising stent-graft 10 in the compressed configuration and outer sheath 22 overlying the stent graft, as shown in FIG. 1. Outer sheath 22 is retracted in the downstream direction such that when first graft segment 14a is completely unsheathed, the intraluminal fluid flows in path B through stent 12 between the sheath and the downstream end 18a of graft segment 14a until upstream end 16b of graft segment 14b is unsheathed sufficiently to cut off flow through path B. The intraluminal fluid then flows through a second path (not shown) through stent 12 between sheath 22 downstream end 18b of the graft segment 14b and the sheath, once graft segment 14b is completely unsheathed. The method comprises continuing to retract outer sheath 22 until stent-graft 10 is fully deployed. In the embodiment shown in FIGS. 1-5, the plurality of graft segments 14a-d overlap one another to create a fluid tight seal at each interface between overlapping graft segments, creating a continuous fluid conduit. In other stent-graft embodiments, such as shown in FIGS. 7 and 9, open areas between axially adjacent graft segments may be aligned with one or more branch lumens.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. A stent-graft comprising:
a single continuous expandable stent of a particular length having a radially compressed configuration and a radially expanded configuration, the stent defining a single continuous lumen with a larger diameter in the radially expanded configuration than in the radially compressed configuration; and
a plurality of discrete and separate grafts in series, each graft lining a different portion of the expandable stent, as determined by being longitudinally displaced along the particular length, and having a first distal upstream end attached to the stent and a second proximal downstream end not attached to the stent, wherein the grafts radially overlie the stent and at least two axially adjacent grafts partially overlap one another to form an overlapped portion on the single continuous expandable stent.

2. The stent-graft of claim 1, wherein each of the plurality of grafts has at least one end that overlaps or is overlapped by an end of an axially adjacent graft.

3. The stent-graft of claim 1, wherein the stent comprises a self-expanding material.

4. The stent-graft of claim 3, wherein the self-expanding material comprises nitinol.

5. The stent-graft of claim 1, wherein the stent comprises a balloon-expanding material.

6. The stent-graft of claim 5, wherein the balloon-expandable material comprises stainless steel.

7. The stent-graft of claim 1, wherein the graft comprises a material selected from the group consisting of: polyethyleneterepthalate (PET), polyetheretherketone (PEEK), polysulfone, polytetrafluroethylene (PTFE), expanded polytetrafluroethylene (ePTFE), fluorinated ethylene propylene (FEP), polycarbonate urethane, a polyolefin, silicone, and polyurethane.

8. The stent graft of claim 7, wherein the graft comprises a polyolefin selected from the group consisting of: polypropylene, polyethylene, or high density polyethylene (HDPE).

9. The stent-graft of claim 1, wherein the stent-graft is adapted for treatment of a thoracic aortic aneurysm.

10. A stent-graft comprising:
a single continuous expandable stent of a particular length having a radially compressed configuration and a radially expanded configuration, the stent defining a single continuous lumen with a larger diameter in the radially expanded configuration than in the radially compressed configuration; and
a plurality of discrete and separate graft segments in series, each graft segment lining a different portion of the expandable stent, as determined by being longituinally displaced along the particular length, and giving a first distal end attached to the stent and a second proximal end not attached to the stent wherein the plurality of graft segments comprises one or more relatively shorter length graft segments and one or more relatively longer length graft segments and wherein the grafts radially overlie the stent and at least two axially adjacent grafts partially overlap one another to form an overlapped portion on the single continuous expandable stent.

11. The stent-graft of claim 10, wherein the stent-graft is adapted for deployment in a body lumen having a curved or tortuous portion with one or more relatively shorter-length graft segments positioned to align with the curved or tortuous portion of the body lumen.

12. A stent-graft comprising:
a single continuous expandable stent of a particular length having a radially compressed configuration and a radially expanded configuration, the stent defining a single continuous lumen with a larger diameter in the radially expanded configuration than in the radially compressed configuration; and
a plurality of discrete and separate grafts in series, each graft lining a different portion of the expandable stent, as determined by being longitudinally displaced along the particular length, and having a first distal end attached to the stent and a second proximal end not attached to the stent, wherein at least a portion of the stent between at least two of the plurality of grafts is not radially overlaid by the at least two of the plurality of grafts.

13. The stent-graft of claim 12, wherein the portion of the stent that is not radially overlaid by a graft segment is an end of the stent adapted to be positioned upstream relative to the rest of the stent-graft in a body lumen having fluid flowing downstream from an upstream location.

14. The stent-graft of claim 1, wherein the overlap extends along less than an entire periphery of the stent-graft.

15. The stent-graft of claim 1, wherein the stent-graft has a central axis and at least one graft has at least one end that has a bias to the central axis.

16. A stent-graft comprising:
a single continuous expandable stent of a particular length having a radially compressed configuration and a radially expanded configuration, the stent defining a single continuous lumen with a larger diameter in the radially expanded configuration than in the radially compressed configuration; and
a plurality of discrete and separate grafts in series, each graft lining a different portion of the expandable stent, as determined by being longitudinally displaced along the particular length, and having a first end attached to the stent and a second end not attached to the stent, wherein the stent-graft has a central axis and at least one graft has at least one end that has an angular bias to the central axis, wherein the angular bias creates a discontinuity between two axially adjacent grafts that partially overlap.

17. A stent-graft comprising a single continuous expandable stent of a particular length and a plurality of discrete and separate graft segments in series, each graft segment lining a different portion of the expandable stent, as determined by being longitudinally displaced along the particular length, and having a first distal end attached to the stent and a second proximal end not attached, wherein the stent-graft has a central axis and at least one graft segment has at least one end that has an angular bias to the central axis, wherein the angular bias creates an opening between two axially adjacent graft segments that partially overlap, the opening defined by a first graft segment having a first angular bias and a second graft segment having a second angular bias not equal to the first bias.

18. The stent-graft of claim 17, wherein the second bias opposes the first bias.

19. The stent-graft of claim 18 wherein the second bias is approximately equal in absolute value to the first bias.

20. A stent-graft comprising:
a single continuous expandable stent of a particular length having a radially compressed configuration and a radially expanded configuration, the stent defining a single continuous lumen with a larger diameter in the radial expanded configuration than in the radially compressed configuration; and
a plurality of discrete and separate graft segments in series, each graft segment lining a different portion of the expandable stent, as determined by being longitudinally displaced along the particular length, and having a first distal end attached to the stent and a second proximal end not attached wherein the stent-graft comprises at least one gap between axially adjacent graft segments, creating a discontinuity in the plurality of graft segments, wherein at least one of the axially adjacent graft segments partially overlaps with another graft segment upstream or downstream from the at least one gap.

21. A stent-graft comprising:
a single continuous expandable stent of a particular length having a radially compressed configuration and a radially expanded configuration, the stent defining a single continuous lumen with a larger diameter in the radially expanded configuration than in the radially compressed configuration; and
a plurality of discrete and separate graft segments in series, each graft segment lining a different portion of the expandable stent, as determined by being longitudinally displaced along the particular length, and having a first distal end attached to the stent and a second proximal end not attached to the stent wherein the plurality of graft segments has at least one discontinuity comprising an opening between axially adjacent graft segments in the plurality of graft segments, wherein at least one of the axially adjacent graft segments partially overlaps with another graft segment upstream or downstream from the at least one discontinuity.

22. The stent-graft of claim 21, wherein the stent-graft is adapted for deployment in a body lumen having at least one branch and the discontinuity is positioned to align with the branch.

23. A stent-graft adapted for deployment inside a body lumen in a distal deployment location from a proximal access location outside the body lumen, the stent-graft comprising:
- a single continuous expandable stent of a particular length underlying a plurality of discrete and separate graft segments, the stent having a radially compressed configuration and a radially expanded configuration, the stent defining a single continuous lumen with a larger diameter in the radially expanded configuration than in the radially compressed configuration;
- the plurality of discrete and separate grafts being arranged in series, each graft segment lining a different portion of the expandable stent, as determined by being longitudinally displaced along the particular length, and having a first distal upstream end attached to the stent and a second proximal downstream end not attached to the stent;
- a plurality of links at or near the first distal upstream end of each graft segment for linking the stent and the graft segments together; and
- a lapped interface between at least one pair of longitudinally adjacent graft segments in which the second proximal downstream end of a distal graft segment partially axially overlaps the first distal upstream end of a proximal graft segment to create a discontinuity between the axially adjacent graft segments.

24. The stent-graft of claim 23, wherein the stent-graft consists essentially of the plurality of graft segments, the expandable stent, the plurality of links, and the lapped interfaces between the graft segments.

25. A stent-graft adapted for deployment inside a body lumen having fluid therein that flows from an upstream direction to a downstream direction, the stent-graft comprising:
- a single continuous expandable stent of a particular length having a radially compressed configuration and a radially expanded configuration, the stent defining a single continuous lumen with a larger diameter in the radially expanded configuration than in the radially compressed configuration;
- a plurality of discrete and separate grafts in series overlying the stent, each graft lining a different portion of the expandable stent, as determined by being longitudinally displaced along the particular length, each graft having an upstream end and a downstream end and linked to the stent only at or near the upstream end with the downstream end being not attached to the stent, wherein for each graft (a) the downstream end partially overlaps the upstream end of a first axially adjacent graft, (b) the upstream end partially overlaps the downstream end of a second axially adjacent graft, or (c) both.

26. A stent-graft adapted for deployment inside a body lumen having fluid therein that flows from an upstream direction to a downstream direction, the stent-graft comprising:
- a single continuous expandable stent of a particular length having a radially compressed configuration and a radially expanded configuration, the stent defining a single continuous lumen with a larger diameter in the radially expanded configuration than in the radially compressed configuration;
- a first graft having an upstream end and a downstream end, the first graft attached to the stent only at the first graft upstream end and the first graft downstream end not attached to the stent; and
- a second graft, discrete and separate from the first graft, the first and second grafts lining different portions of the expandable stent, as determined by being longitudinally displaced along the particular length, the second graft having an upstream end and attached to the stent only at the second graft upstream end in an axial location that is upstream of the downstream end of the first graft, such that the first graft downstream end partially overlaps the second graft upstream end, and the second graft downstream end is not attached to the stent.

27. The stent-graft of claim 1, wherein the grafts radially underlie the stent.

28. The stent-graft of claim 1, wherein at least one of the plurality of separate grafts has a length different from the remainder of the plurality of separate grafts.

* * * * *